United States Patent
Zribi

(10) Patent No.: US 7,302,829 B2
(45) Date of Patent: Dec. 4, 2007

(54) CONTACTLESS HUMIDITY/CHEMICAL VAPOR SENSOR DEVICE AND ASSOCIATED METHOD OF FABRICATION

(75) Inventor: Anis Zribi, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 701 days.

(21) Appl. No.: 10/726,038

(22) Filed: Dec. 1, 2003

(65) Prior Publication Data

US 2005/0116831 A1    Jun. 2, 2005

(51) Int. Cl.
*G01N 29/00* (2006.01)

(52) U.S. Cl. ............... 73/29.01; 73/23.2; 73/24.01; 73/24.06; 73/31.01; 73/31.05

(58) Field of Classification Search .......... 73/24.01, 73/24.04, 24.06, 23.2, DIG. 2, 29.05, 31.01, 73/31.04, 31.05, 24.02
See application file for complete search history.

(56) References Cited

U.S. PATENT DOCUMENTS

| | | | |
|---|---|---|---|
| 5,821,129 A * | 10/1998 | Grimes et al. | 436/151 |
| 6,359,444 B1 * | 3/2002 | Grimes | 324/633 |
| 6,393,921 B1 * | 5/2002 | Grimes et al. | 73/728 |
| 6,397,661 B1 * | 6/2002 | Grimes et al. | 73/24.06 |
| 2002/0166382 A1 * | 11/2002 | Bachas et al. | 73/579 |
| 2004/0105807 A1 * | 6/2004 | Fan et al. | 423/447.3 |

OTHER PUBLICATIONS

Efremov, M. Yu., "Discrete Periodic Melting Point Observations for Nanostructure Ensembles," Physical Review Letters, vol. 85, No. 17, pp. 3560-3563, Oct. 23, 2000.
Kwan, A.T., "Nanoscale Calorimetry of Isolated Polyethylene Single Crystals," Journal of Polymer Science: Part B: Polymer Physics, vol. 39, pp. 1237-1245, Mar. 22, 2001.

* cited by examiner

*Primary Examiner*—Daniel S. Larkin
(74) *Attorney, Agent, or Firm*—Fletcher Yoder

(57) ABSTRACT

The invention provides a contactless sensor device operable for sensing water vapor or a predetermined chemical vapor including a thin film, wherein the thin film includes a nanostructured sensing layer and a soft magnetic layer disposed directly adjacent to the nanostructured sensing layer. The thin film has a first mass, a first density, and a first magnetostrictive resonance frequency prior to the nanostructured sensing layer adsorbing a predetermined amount of a predetermined vapor and a second mass, a second density, and a second magnetostrictive resonance frequency subsequent to the nanostructured sensing layer adsorbing the predetermined amount of the predetermined vapor. The sensor device also includes a driving coil disposed indirectly adjacent to and at a predetermined distance from the thin film, the driving coil operable for generating an alternating-current magnetic field used to query a shift in the magnetostrictive resonance frequency of the thin film. The sensor device further includes a measuring coil disposed indirectly adjacent to and at a predetermined distance from the thin film, the measuring coil operable for measuring and quantifying the shift in the magnetostrictive resonance frequency of the thin film.

38 Claims, 7 Drawing Sheets

CONTACTLESS HUMIDITY/CHEMICAL VAPOR SENSOR DEVICE AND ASSOCIATED METHOD OF FABRICATION

FIELD OF THE INVENTION

The invention relates generally to the field of miniaturized sensor devices and, more specifically, to the field of nanoscale sensor devices. The invention provides a contactless, high-sensitivity, high-selectivity, high-stability, fast-response humidity or chemical vapor sensor device, among other sensor devices, and an associated method of fabrication. Advantageously, the humidity or chemical vapor sensor device of the invention is suitable for use in, for example, security and warfare sensing applications.

BACKGROUND OF THE INVENTION

The scientific and technological interest in miniaturized humidity and chemical vapor sensor devices has grown in recent years. The need for such sensor devices spans a wide range of industries and applications, such as the medical instrumentation, food and agriculture, paper, automotive, electric appliance, petrochemical, fuel cell, and semiconductor industries, as well as the military, in, for example, humidity, chemical vapor, organic vapor, and gas sensing applications. The wide range of environments that these sensor devices may be exposed to severely limits the candidate materials that may be used to build the sensor devices. A number of humidity and chemical vapor sensor devices have been developed and built for specific applications. However, none of these sensor devices demonstrates a suitable combination of the desired robustness, sensitivity, selectivity, stability, size, simplicity, reproducibility, reliability, response time, resistance to contaminants, and longevity. Thus, what are still needed are humidity and chemical vapor sensor devices, among other sensor devices, that exploit the high sensitivity of the magnetostrictive resonance frequency of soft magnetic thin films to changes in mass and the unique properties of certain porous nanostructured thin films, nanoparticles, nanorods, nanotubes, and nanofibers, including their high adsorption potential, high adsorption rate, high desorption rate, high chemical stability, and heat release characteristics associated with the physisorption of water vapor and chemical vapor molecules.

BRIEF SUMMARY OF THE INVENTION

In various embodiments, the invention provides a contactless, high-sensitivity, high-selectivity, high-stability, fast-response humidity or chemical vapor sensor device, among other sensor devices, and an associated method of fabrication. The humidity or chemical vapor sensor device of the invention exploits the high sensitivity of the magnetostrictive resonance frequency of soft magnetic thin films, such as $Fe(x)Ni(y)P(z)B(n)$, $Fe(x)Tb(y)Dy(z)$, and $Fe(x)Si(y)$ thin films and the like, to changes in mass and the unique properties of certain porous nanostructured thin films, nanoparticles, nanorods, nanotubes, and nanofibers of materials, such as zeolites, polyelectrolytes, porous ceramics, aluminosilicates, carbon, and the like, including their high adsorption potential, high adsorption rate, high desorption rate, high chemical stability, and heat release characteristics associated with the physisorption of water vapor and chemical vapor molecules.

In one specific embodiment of the invention, a contactless sensor device operable for sensing water vapor or a predetermined chemical vapor includes a thin film, wherein the thin film includes a nanostructured or self-assembled monomolecular sensing layer and a soft magnetic layer disposed directly or indirectly adjacent to the sensing layer. Optionally, an adhesion layer, such as a polymer (epoxy, glue, etc.) layer, a metal (Au, Ti, Cr, Pt, Al, etc.) layer, or the like, is intercalated between the sensing layer and the soft magnetic layer to promote adhesion at this interface. The thin film has a first mass, a first density, and a first magnetostrictive resonance frequency prior to the sensing layer adsorbing a predetermined amount of a predetermined vapor. The thin film has a second mass, a second density, and a second magnetostrictive resonance frequency subsequent to the sensing layer adsorbing the predetermined amount of the predetermined vapor. The sensor device also includes a driving coil, external to the device, disposed indirectly adjacent to and at a predetermined distance from the thin film, the driving coil operable for generating an alternating-current magnetic field used to query a shift in the magnetostrictive resonance frequency of the thin film from the first magnetostrictive resonance frequency to the second magnetostrictive resonance frequency. The sensor device further includes a measuring coil, external to the device, disposed indirectly adjacent to and at a predetermined distance from the thin film, the measuring coil operable for measuring and quantifying the shift in the magnetostrictive resonance frequency of the thin film from the first magnetostrictive resonance frequency to the second magnetostrictive resonance frequency.

In another specific embodiment of the invention, a method for fabricating a contactless sensor device operable for sensing water vapor or a predetermined chemical vapor includes providing a thin film, wherein providing the thin film includes providing a soft magnetic layer and disposing a nanostructured or self-assembled monomolecular sensing layer directly or indirectly adjacent to the soft magnetic layer. Optionally, an adhesion layer, such as a polymer (epoxy, glue, etc.) layer, a metal (Au, Ti, Cr, Pt, Al, etc.) layer, or the like, is intercalated between the sensing layer and the soft magnetic layer to promote adhesion at this interface. The thin film has a first mass, a first density, and a first magnetostrictive resonance frequency prior to the sensing layer adsorbing a predetermined amount of a predetermined vapor. The thin film has a second mass, a second density, and a second magnetostrictive resonance frequency subsequent to the sensing layer adsorbing the predetermined amount of the predetermined vapor. The method also includes disposing a driving coil indirectly adjacent to and at a predetermined distance from the thin film, the driving coil operable for generating an alternating-current magnetic field used to query a shift in the magnetostrictive resonance frequency of the thin film from the first magnetostrictive resonance frequency to the second magnetostrictive resonance frequency. The method further includes disposing a measuring coil indirectly adjacent to and at a predetermined distance from the thin film, the measuring coil operable for measuring and quantifying the shift in the magnetostrictive resonance frequency of the thin film from the first magnetostrictive resonance frequency to the second magnetostrictive resonance frequency.

In a further specific embodiment of the invention, the contactless sensor device operable for sensing water vapor or a predetermined chemical vapor incorporates one or more microheater devices sandwiched between a plurality of dielectric layers, such as two silicon nitride layers, two silicon oxide layers, two parylene layers, two polyimide layers, or the like. The one or more microheater devices are operable for rapidly removing the adsorbate from the sensing layer in order to rapidly refresh the transducer and prepare it for subsequent measurements. The sensing layer and the soft magnetic layer are disposed on opposing sides of the dielectric/microheater/dielectric sandwich. The one or more microheater devices are powered in a contactless manner using, among other contactless power sources, mutually induced currents generated in an antenna integrated on the substrate of the sensor device, solar energy (for security and warfare sensing applications), and/or the like. The one or more microheater devices are made of a metal thin film, a heavily-doped silicon thin film, a silicon carbide thin film, or the like.

In a still further specific embodiment of the invention, a contactless microelectromechanical (MEMS) sensor device operable for sensing water vapor or a predetermined chemical vapor includes a thin film, wherein the thin film includes a nanostructured or self-assembled monomolecular sensing layer and a soft magnetic layer disposed directly or indirectly adjacent to the sensing layer. Optionally, an adhesion layer, such as a polymer (epoxy, glue, etc.) layer, a metal (Au, Ti, Cr, Pt, Al, etc.) layer, or the like, is intercalated between the sensing layer and the soft magnetic layer to promote adhesion at this interface. The thin film has a first mass, a first density, and a first magnetostrictive resonance frequency prior to the sensing layer adsorbing a predetermined amount of a predetermined vapor. The thin film has a second mass, a second density, and a second magnetostrictive resonance frequency subsequent to the sensing layer adsorbing the predetermined amount of the predetermined vapor. The thin film is either sputtered onto a silicon or alumina substrate one layer at a time or, alternatively, is integrated together with a microelectromechanical (MEMS) device using standard microelectromechanical (MEMS) packaging technologies, well known to those of ordinary skill in the art. The microelectromechanical (MEMS) device encompasses one or a plurality of integrated microcoils, including, for example, both planar and out-of-plane microcoils. At least one of these microcoils is used to query shifts in the magnetostrictive resonance frequency of the thin film, at least one of the microcoils is used to measure these shifts in the magnetostrictive resonance frequency of the thin film, and at least one of the microcoils operates as an antenna for transmitting the resulting data to an external contactless data logger. Other processing and data transmission electronics may, however, be used to acquire, process, and transmit the data in a contactless manner.

DETAILED DESCRIPTION OF THE INVENTION

In various embodiments, the invention provides a contactless, high-sensitivity, high-selectivity, high-stability, fast-response humidity or chemical vapor sensor device, among other sensor devices, and an associated method of fabrication. The humidity or chemical vapor sensor device of the invention exploits the high sensitivity of the magnetostrictive resonance frequency of soft magnetic thin films, such as $Fe(x)Ni(y)P(z)B(n)$, $Fe(x)Tb(y)Dy(z)$, and $Fe(x)Si(y)$ thin films and the like, to changes in mass and the unique properties of certain porous nanostructured thin films, nanoparticles, nanorods, nanotubes, and nanofibers of materials, such as zeolites, polyelectrolytes (such as polystyrene sulfonic acid and the like), porous ceramics, aluminosilicates, carbon, and the like, including their high adsorption potential, high adsorption rate, high desorption rate, high chemical stability, and heat release characteristics associated with the physisorption of water vapor and chemical vapor molecules.

Figure 1:
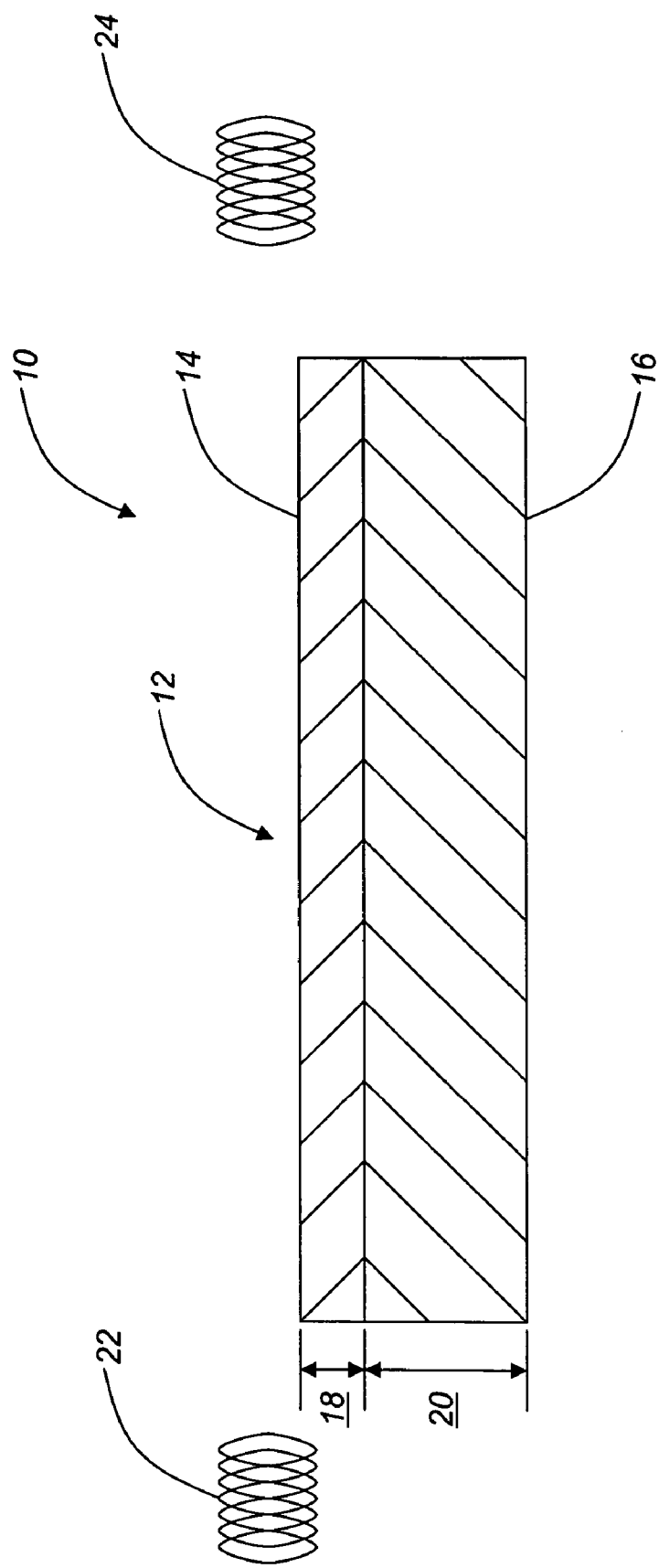
FIG. 1 is a cross-sectional side view of one embodiment of the humidity or chemical vapor sensor device, among other sensor devices, of the invention, highlighting the use of a thin film, including a nanostructured or self-assembled monomolecular sensing layer and a soft magnetic layer, a driving coil, and a measuring coil.
Figure 2:
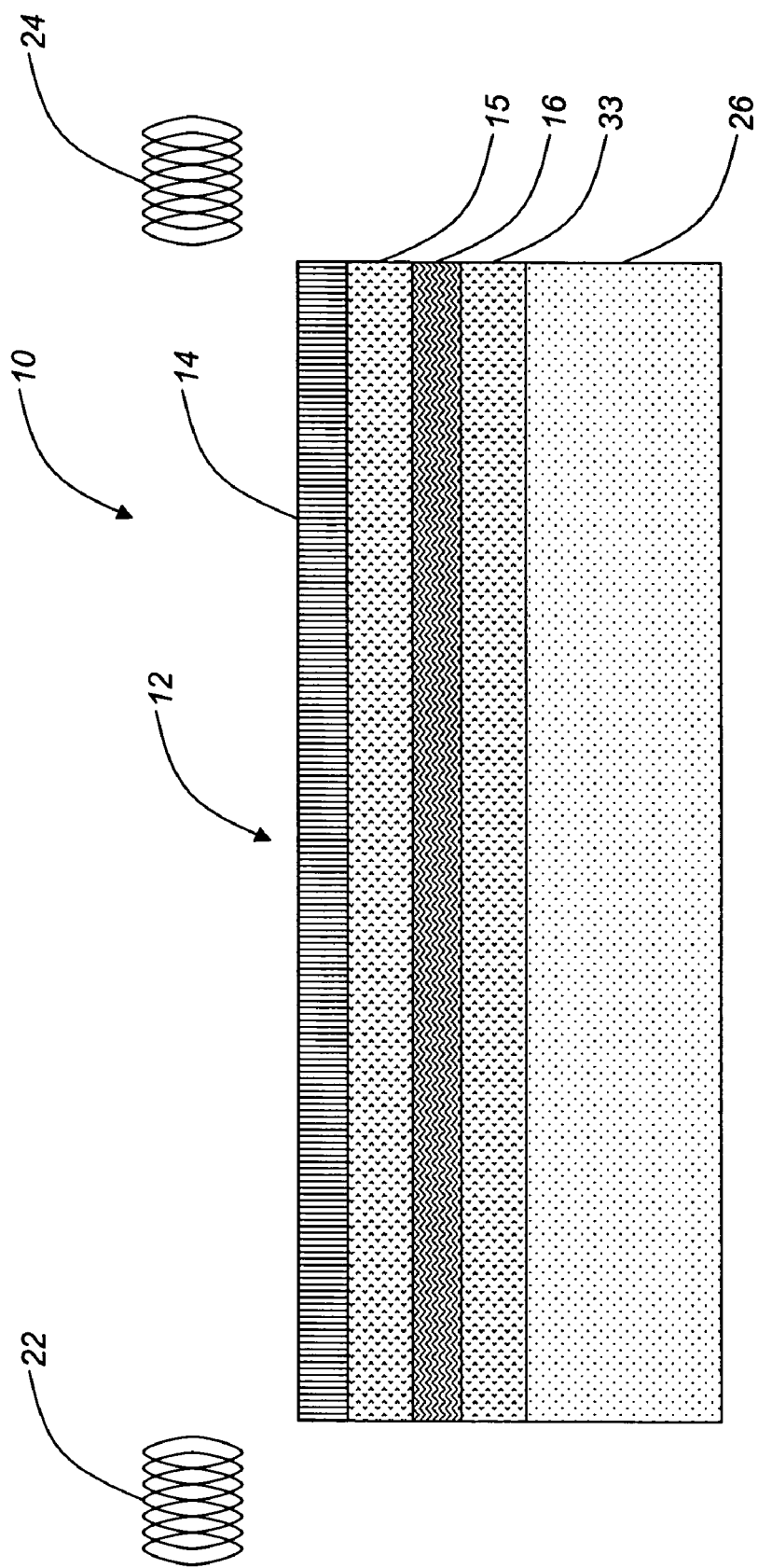
FIG. 2 is a cross-sectional side view of another embodiment of the humidity or chemical vapor sensor device, among other sensor devices, of the invention, highlighting the use of a thin film, including a nanostructured or self-assembled monomolecular sensing layer, a soft magnetic layer, and an adhesion layer, a driving coil, a measuring coil, and a substrate.
Figure 3:
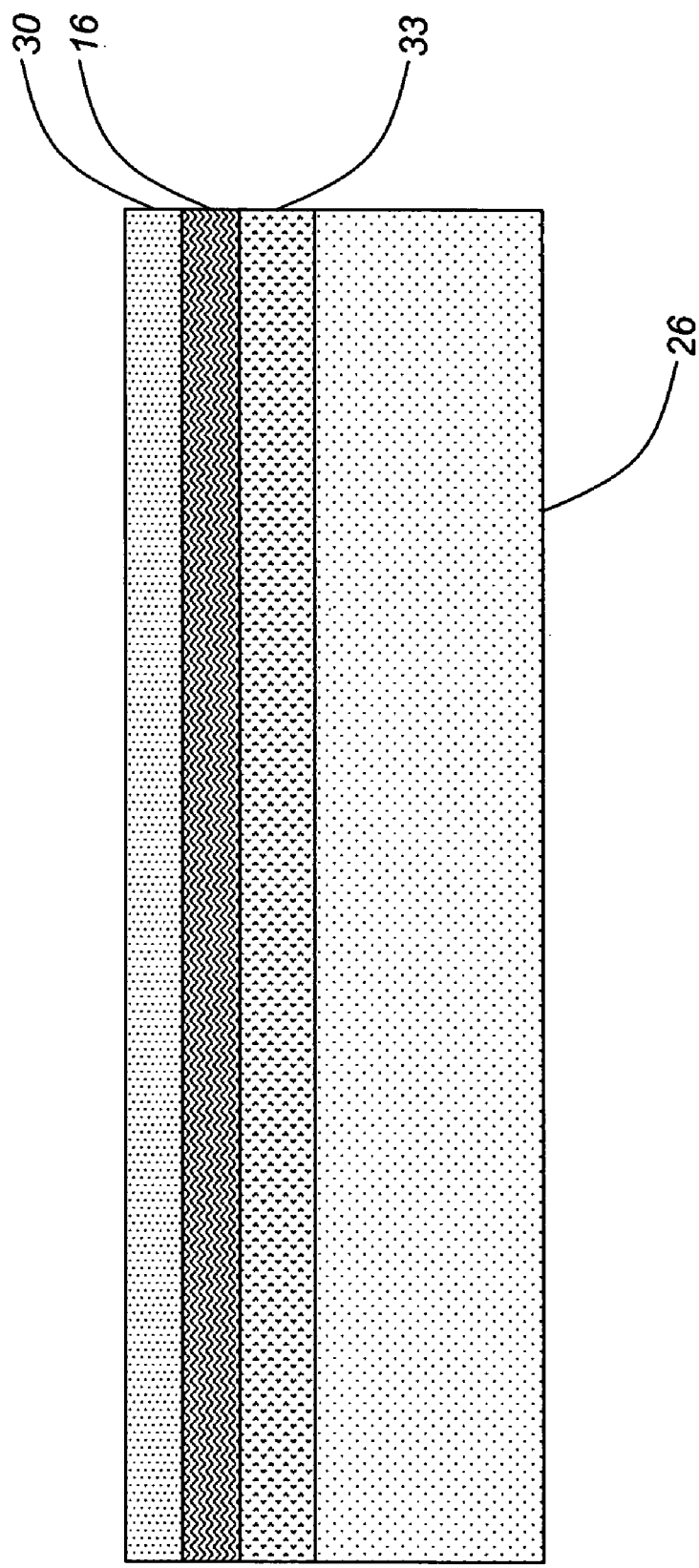
FIG. 3 is a cross-sectional side view of a further embodiment of the humidity or chemical vapor sensor device, among other sensor devices, of the invention, highlighting the addition of a thin dielectric layer and a soft magnetic layer to a substrate.
Figure 4:
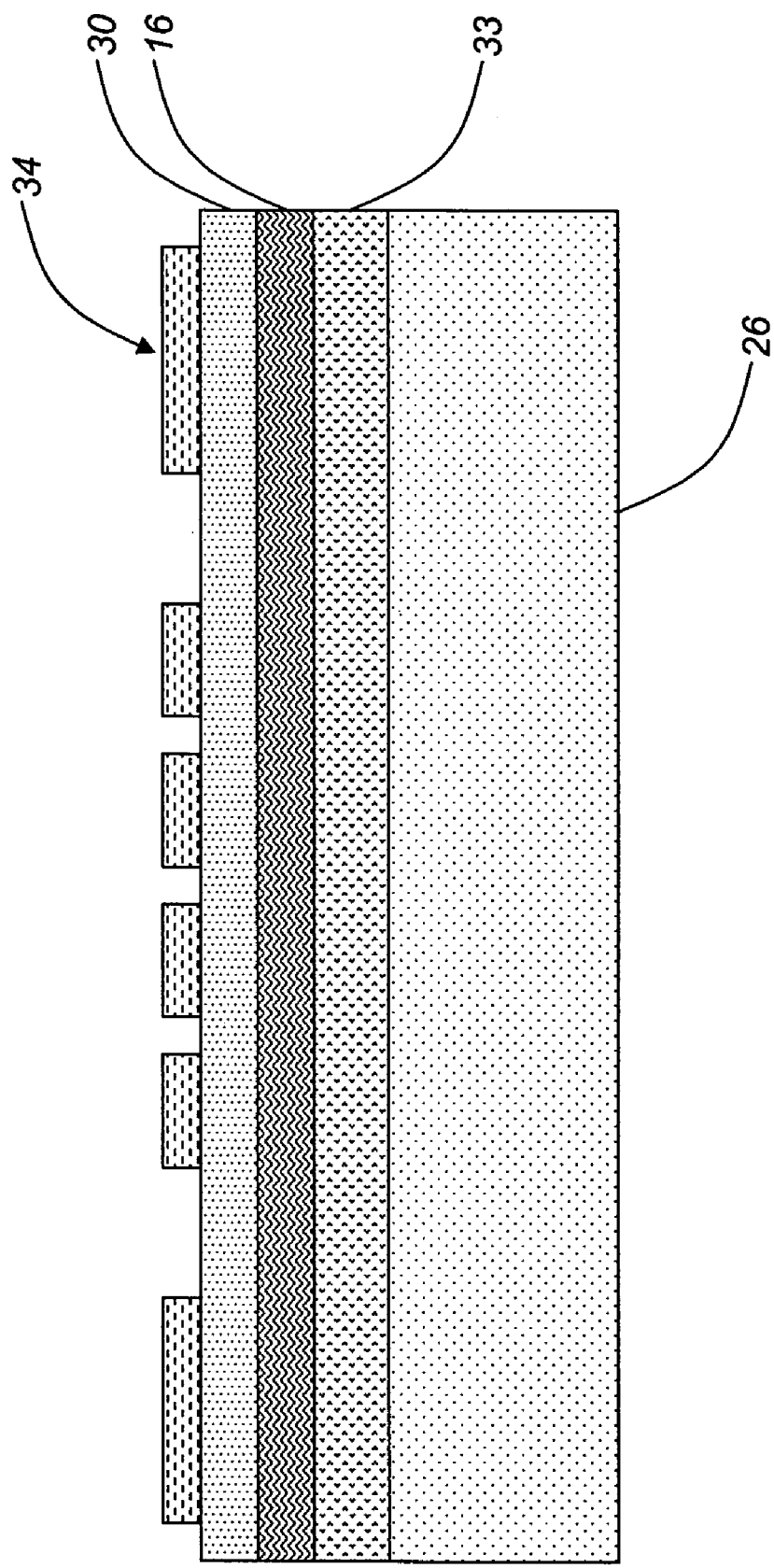
FIG. 4 is a cross-sectional side view of the humidity or chemical vapor sensor device of FIG. 3, highlighting the patterning and addition of one or more thin film microheater devices to the exposed surface of the previously deposited thin dielectric layer.
Figure 5:
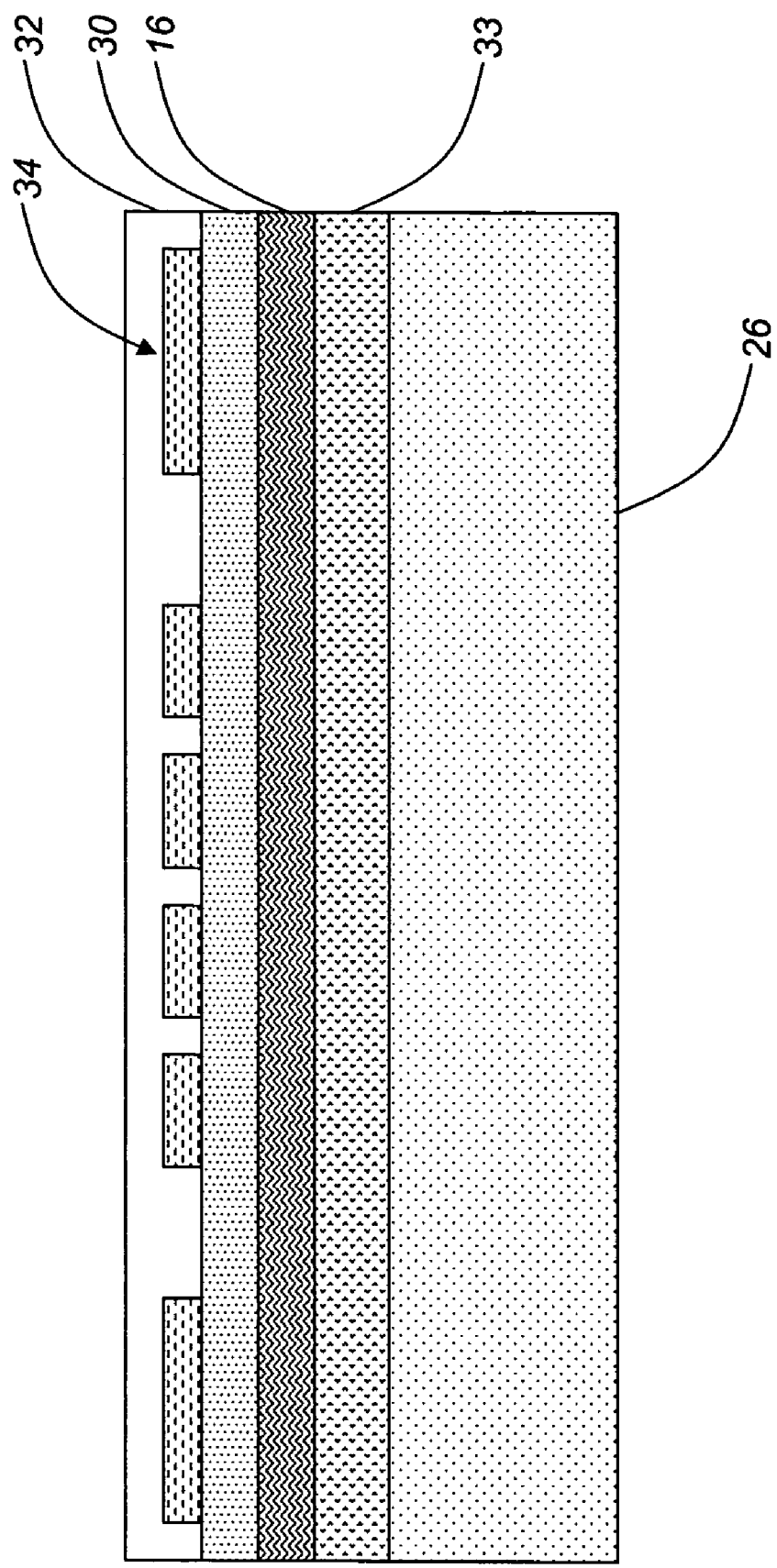
FIG. 5 is a cross-sectional side view of the humidity or chemical vapor sensor device of FIG. 4, highlighting the addition of an additional thin dielectric layer to the exposed surface of the previously deposited thin dielectric layer and the exposed surfaces of the one or more microheater devices.
Figure 6:
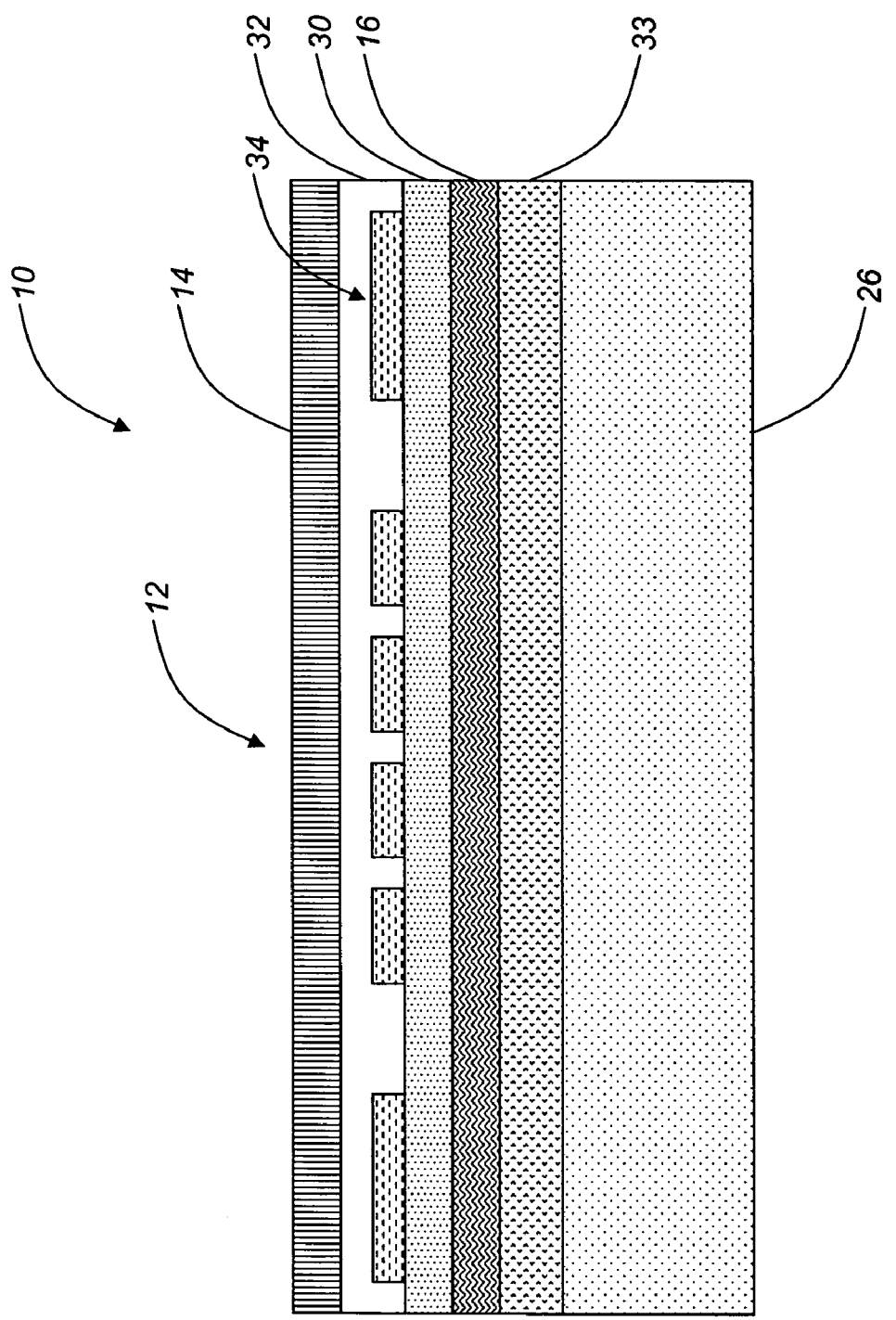
FIG. 6 is a cross-sectional side view of the humidity or chemical vapor sensor device of FIG. 5, highlighting the addition of a nanostructured or self-assembled monomolecular sensing layer to the exposed surface of the previously deposited additional thin dielectric layer.

Referring to FIG. 1, the humidity or chemical vapor sensor device 10 of the invention includes a thin film 12 including a nanostructured or self-assembled monomolecular sensing layer 14 disposed directly or indirectly adjacent to a soft magnetic layer 16. Referring to FIG. 2, optionally, an adhesion layer 15, such as a polymer (epoxy, glue, etc.) layer, a metal (Au, Ti, Cr, Pt, Al, etc.) layer, or the like, is intercalated between the nanostructured or self-assembled monomolecular sensing layer 14 and the soft magnetic layer 16 to promote adhesion at this interface. Preferably, the nanostructured or self-assembled monomolecular sensing layer 14 includes a zeolite thin film or a layer of zeolite nanoparticles, a polyelectrolyte thin film or a layer of polyelectrolyte nanoparticles (such as a polystyrene sulfonic acid thin film or a layer of polystyrene sulfonic acid nanoparticles), a porous ceramic thin film or a layer of porous ceramic nanoparticles, an aluminosilicate thin film or a layer of aluminosilicate nanoparticles, or the like. In general, the nanostructured or self-assembled monomolecular sensing layer 14 demonstrates high adsorption potential, high adsorption rate, high desorption rate, high chemical stability, and heat release characteristics associated with the physisorption of water vapor and chemical vapor molecules. Advantageously, the microstructure and pore dimensions of the nanostructured or self-assembled monomolecular sensing layer 14 may be customized to ensure the high selectivity of the humidity or chemical vapor sensor device towards water vapor molecules or predetermined chemical vapor molecules versus other vapor molecules that may be present in the environment. For example, the pore dimensions of the nanostructured or self-assembled monomolecular sensing layer 14 may be on the order of between about 0.3 nm and about 1 nm. Preferably, the soft magnetic layer 16 is thin film-like or ribbon-like and includes $Fe(x)Ni(y)P(z)B(n)$, $Fe(x)Tb(y)Dy(z)$, $Fe(x)Si(y)$, or the like. In general, the soft magnetic layer 16 demonstrates high magnetostriction and expands or contracts in the presence of a magnetic field, causing the thin film 12 to deform. Preferably, the nanostructured or self-assembled monomolecular sensing layer 14 has an initial thickness 18 of between about 1 nm and about 1 mm, although other suitable dimensions may be used. Preferably, the soft magnetic layer 16 has an initial thickness 20 of between about 100 nm and about 1 mm, although other suitable dimensions may be used. Referring again to FIG. 2, the nanostructured or self-assembled monomolecular sensing layer 14 and the soft magnetic layer 16 may be disposed on (directly or indirectly adjacent to) the surface of a substrate 26, such as a silicon substrate, an alumina substrate, or the like.

In one exemplary embodiment of the invention, the soft magnetic layer 16 is formed by sputtering or casting from a melt. The nanostructured or self-assembled monomolecular sensing layer 14 is grown or deposited on the surface of the soft magnetic layer 16 by, for example, a direct growth technique, spin casting, physical vapor deposition, a Langmuir-Blodgett self-assembled monomolecular layer deposition method, or another self-assembled monomolecular layer deposition method. Advantageously, this provides a direct interface between the nanostructured or self-assembled monomolecular sensing layer 14 and the soft magnetic layer 16 and prevents delamination. As described above, if poor adhesion or delamination presents a problem, an adhesion layer 15,33 (FIG. 2), such as a polymer (epoxy, glue, etc.) layer, a metal (Au, Ti, Cr, Pt, Al, etc.) layer, or the like, may be intercalated between the nanostructured or self-assembled monomolecular sensing layer 14 and the soft magnetic layer 16 and/or the soft magnetic layer 16 and the substrate 26 to promote adhesion at these interfaces.

Figure 7:
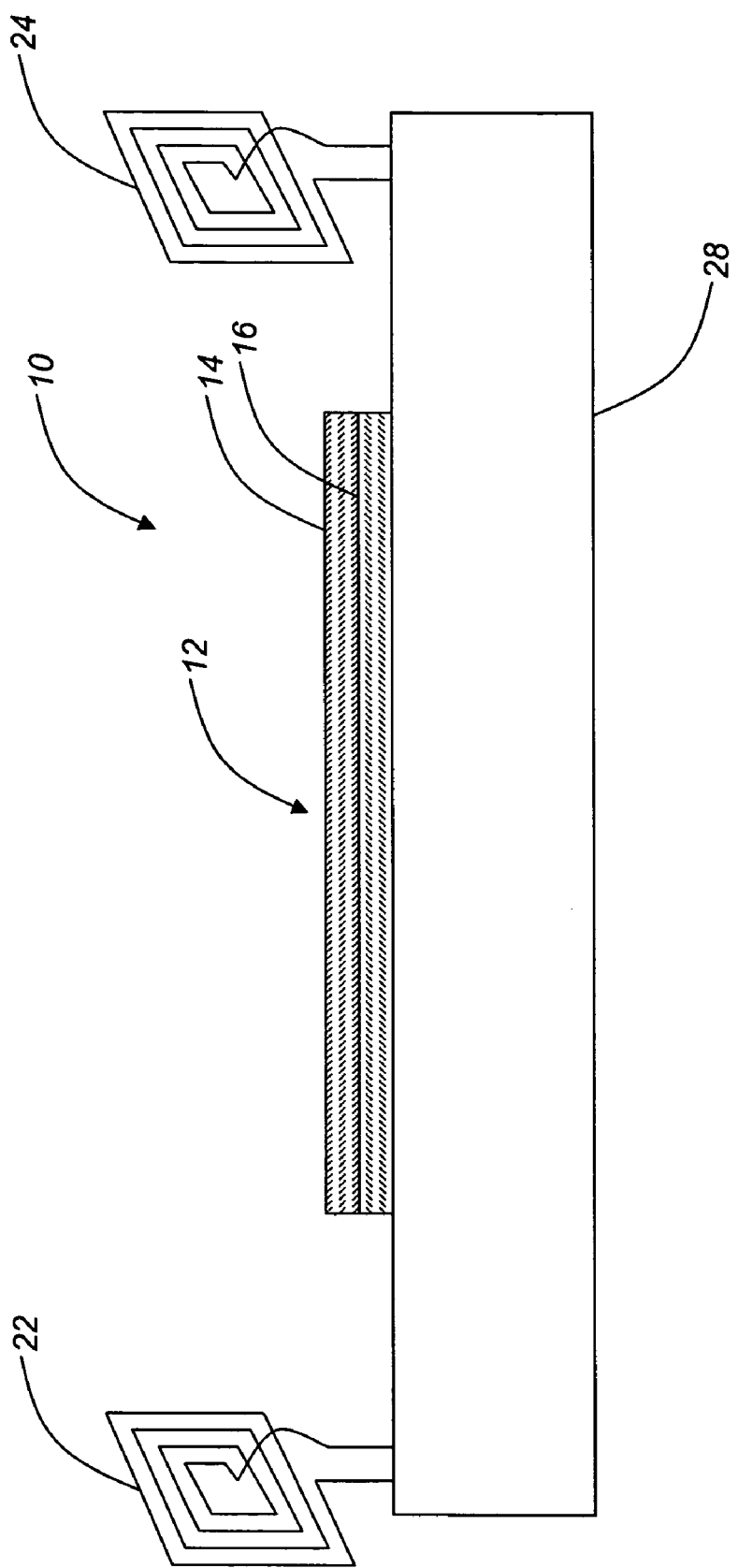
FIG. 7 is a cross-sectional side view of a still further embodiment of the humidity or chemical vapor sensor device, among other sensor devices, of the invention, highlighting the integration of the transducer of FIG. 1 with an on-chip driving coil, measuring coil, and transmitting coil.

A driving coil 22 and a measuring coil 24 are each disposed indirectly adjacent to and at a predetermined distance from the thin film 12. Optionally, the driving coil 22 and the measuring coil 24 each consists of a planar coil integrated on a silicon wafer 28 or the like, as illustrated in FIG. 7. Preferably, the driving coil 22 and the measuring coil 24 are each disposed at an initial distance of between about 1 cm and about 0.5 m from the thin film 12, although other suitable distances may be used. The driving coil 22 is operable for generating an alternating-current (AC) magnetic field used to query a shift in the magnetostrictive resonance frequency of the thin film 12 when the nanostructured or self-assembled monomolecular sensing layer 14 adsorbs water vapor or a predetermined chemical vapor. The measuring coil 24 is operable for measuring and quantifying this shift in the magnetostrictive resonance frequency of the thin film 12.

For example, upon the adsorption of a given amount of a specific vapor onto the surface of the zeolite layer, the mass of the thin film 12 changes by a given amount (e.g., from a first mass to a second mass). This change in mass induces an increase in the density of the thin film 12 (e.g., from a first density to a second density) and a corresponding shift in the magnetostrictive resonance frequency of the thin film 12 (e.g., from a first magnetostrictive resonance frequency to a second magnetostrictive resonance frequency), driven by the driving coil 22. This shift in magnetostrictive resonance frequency may be obtained using both the driving coil 22 and the measuring coil 24. In general, magnetic energy is converted into elastic energy that leads to the deformation of the thin film 12 and magnetic flux emission. The driving coil 22 is used to sweep an alternating-current (AC) magnetic field used to query the humidity or chemical vapor sensor device 10 and the response of the thin film 12. The thin film 12 is in magnetostrictive resonance when the frequency of the driving alternating-current (AC) magnetic field is equal to the magnetostrictive resonance frequency of the thin film 12. The measuring coil 24 measures the frequency of the magnetic flux emitted by the thin film 12 and a network analyzer, for example, is used to determine the frequency shift.

Referring to FIGS. 3-6, in an alternative embodiment, the humidity or chemical vapor sensor device 10 of the invention includes a thin film 12 including a nanostructured or self-assembled monomolecular sensing layer 14 disposed indirectly adjacent to a soft magnetic layer 16. Preferably, the nanostructured or self-assembled monomolecular sensing layer 14 includes a zeolite thin film or a layer of zeolite nanoparticles, a polyelectrolyte thin film or a layer of polyelectrolyte nanoparticles (such as a polystyrene sulfonic acid thin film or a layer of polystyrene sulfonic acid nanoparticles), a porous ceramic thin film or a layer of porous ceramic nanoparticles, an aluminosilicate thin film or a layer of aluminosilicate nanoparticles, or the like. In general, the nanostructured or self-assembled monomolecular sensing layer 14 demonstrates high adsorption potential, high adsorption rate, high desorption rate, high chemical stability, and heat release characteristics associated with the physisorption of water vapor and chemical vapor molecules. Advantageously, the microstructure and pore dimensions of the nanostructured or self-assembled monomolecular sensing layer 14 may be customized to ensure the high selectivity of the humidity or chemical vapor sensor device towards water vapor molecules or predetermined chemical vapor molecules versus other vapor molecules that may be present in the environment. For example, the pore dimensions of the nanostructured or self-assembled monomolecular sensing layer 14 may be on the order of between about 0.3 nm and about 1 nm. Preferably, the soft magnetic layer 16 is thin film-like or ribbon-like and includes $Fe(x)Ni(y)P(z)B(n)$, $Fe(x)Tb(y)Dy(z)$, $Fe(x)Si(y)$, or the like. In general, the soft magnetic layer 16 demonstrates high magnetostriction and expands or contracts in the presence of a magnetic field, causing the thin film 12 to deform. Preferably, the nanostructured or self-assembled monomolecular sensing layer 14 has an initial thickness 18 of between about 1 nm and about 1 mm, although other suitable dimensions may be used. Preferably, the soft magnetic layer 16 has an initial thickness 20 of between about 100 nm and about 1 mm, although other suitable dimensions may be used. The nanostructured or self-assembled monomolecular sensing layer 14 and the soft magnetic layer 16 may be disposed on (directly or indirectly adjacent to) the surface of a substrate 26, such as a silicon substrate, an alumina substrate, or the like.

A plurality of dielectric layers 30, 32 is disposed between the nanostructured or self-assembled monomolecular sensing layer 14 and the soft magnetic layer 16. The plurality of dielectric layers 30, 32 each consists of a silicon nitride layer, a silicon oxide layer, a parylene layer, a polyimide layer, or the like. Preferably, one or more microheater devices 34 are sandwiched between the plurality of dielectric layer 30, 32 and, thus, between the nanostructured or self-assembled monomolecular sensing layer 14 and the soft magnetic layer 16. The one or more microheater devices 34 each consist of a metal thin film, a heavily-doped silicon thin film, a silicon carbide thin film, or the like. Advantageously, the one or more microheater devices 34 are operable for rapidly removing the adsorbate from the nanostructured or self-assembled monomolecular sensing layer 14 to rapidly refresh the transducer and prepare it for subsequent measurements. The one or more microheater devices 34 are powered in a contactless manner using, among other contactless power sources, mutually induced currents generated in an antenna integrated on the substrate 26 of the sensor device 10, solar energy (for security and warfare sensing applications), and/or the like.

The humidity or chemical vapor sensor device 10 (FIGS. 1, 2, 6, 7) of the invention also includes a correlation algorithm (not shown), which may consist of software residing in a computer or the like, operable for correlating the measured and quantified shift in the magnetostrictive resonance frequency of the thin film 12 to an amount of the water vapor or predetermined chemical vapor present in the environment surrounding the humidity or chemical sensor device 10.

The humidity or chemical vapor sensor device 10 (FIGS. 1, 2, 6, 7) of the invention may be used in a variety of applications, including security and warfare sensing applications. Examples of such security and warfare sensing applications include, but are not limited to, baggage and cargo screening for explosives and chemical agents. The humidity or chemical vapor sensor device 10 of the invention may also be used in the following exemplary applications: humidity or toxic gas monitoring for the ventilation systems of structures, emissions monitoring for automotive engine control, environmental conditions monitoring for shipping containers, hazardous or bio-warfare agent monitoring for transportation security, humidity monitoring for appliances, fire detection and response systems, disposable weather monitoring and forecasting systems, measuring the alcohol content of a human's breath, minimally-invasive blood glucose monitoring systems, monitoring human airways gas for medical and disease diagnosis, food and agricultural packaging and shipping systems, monitoring on-chip humidity for electronic circuits, monitoring humidity or chemical leaks for pressure vessels and containers, immobilization and manipulation systems for cells and proteins, medical instrumentation systems, paper production systems, semiconductor process monitoring systems, natural resource exploration and development systems, and the like.

Although the invention has been illustrated and described with reference to preferred embodiments and examples thereof, it will be readily apparent to those of ordinary skill in the art that other embodiments and examples may perform similar functions and/or achieve similar results. All such equivalent embodiments and examples are within the spirit and scope of the invention and are intended to be covered by the following claims.

What is claimed is:

1. A contactless sensor device operable for sensing water vapor or a predetermined chemical vapor, the sensor device comprising:
    a thin film, wherein the thin film comprises:
        a sensing layer, wherein the sensing layer comprises one of a nanostructured layer and a self-assembled monomolecular layer;
        a soft magnetic layer disposed directly or indirectly adjacent to the sensing layer;
        wherein the thin film has a first mass, a first density, and a first magnetostrictive resonance frequency prior to the sensing layer adsorbing a predetermined amount of a predetermined vapor; and
        wherein the thin film has a second mass, a second density, and a second magnetostrictive resonance frequency subsequent to the sensing layer adsorbing the predetermined amount of the predetermined vapor;
    at least one microheater disposed between the sensing layer and the soft magnetic layer;
    a driving coil disposed indirectly adjacent to and at a predetermined distance from the thin film, the driving coil operable for generating an alternating-current magnetic field used to query a shift in the magnetostrictive resonance frequency of the thin film from the first magnetostrictive resonance frequency to the second magnetostrictive resonance frequency; and
    a measuring coil disposed indirectly adjacent to and at a predetermined distance from the thin film, the measuring coil operable for measuring and quantifying the shift in the magnetostrictive resonance frequency of the thin film from the first magnetostrictive resonance frequency to the second magnetostrictive resonance frequency.

2. The sensor device of claim 1, wherein the thin film has an initial thickness of between about 100 nm and about 5 mm.

3. The sensor device of claim 1, wherein the sensing layer comprises a plurality of nanoparticles.

4. The sensor device of claim 3, wherein the plurality of nanoparticles comprise at least one of a plurality of nanorods, a plurality of nanotubes, and a plurality of nanofibers.

5. The sensor device of claim 1, wherein the sensing layer comprises a material selected from the group consisting of a zeolite, a polyelectrolyte, a porous ceramic, an aluminosilicate, carbon, and a combination comprising at least one of the foregoing materials.

6. The sensor device of claim 1, wherein the sensing layer has an initial thickness of between about 1 nm and about 1 mm.

7. The sensor device of claim 1, wherein the soft magnetic layer comprises a material selected from the group consisting of $Fe(x)Ni(y)P(z)B(n)$, $Fe(x)Tb(y)Dy(z)$, $Fe(x)Si(y)$, and a combination comprising at least one of the foregoing materials.

8. The sensor device of claim 1, wherein the soft magnetic layer has an initial thickness of between about 100 nm and about 1 mm.

9. The sensor device of claim 1, wherein the driving coil and the measuring coil each comprise a planar coil integrated on a silicon wafer.

10. The sensor device of claim 1, wherein the driving coil and the measuring coil are each disposed at an initial distance of between about 1 cm and about 0.5 m from the thin film.

11. The sensor device of claim 1, further comprising a correlation algorithm operable for correlating the measured and quantified shift in the magnetostrictive resonance frequency of the thin film from the first magnetostrictive resonance frequency to the second magnetostrictive resonance frequency to an amount of the predetermined vapor present in an environment surrounding the sensor device.

12. The sensor device of claim 1, wherein the predetermined vapor comprises one of water vapor and a predetermined chemical vapor.

13. The sensor device of claim 1, further comprising an adhesion layer disposed between the sensing layer and the soft magnetic layer, wherein the adhesion layer comprises at least one of a polymer layer and a metal layer.

14. The sensor device of claim 1, further comprising a plurality of dielectric layers disposed between the sensing layer and the soft magnetic layer, wherein the at least one microheater and the plurality of dielectric layers are arranged in a sandwich configuration.

15. The sensor device of claim 14, wherein each of the plurality of dielectric layers comprises a material selected from the group consisting of silicon nitride, silicon oxide, parylene, and polyimide.

16. The sensor device of claim 1, wherein each microheater comprises a material selected from the group consisting of a metal thin film, a heavily-doped silicon thin film, and a silicon carbide thin film.

17. The sensor device of claim 1, further comprising a substrate disposed directly or indirectly adjacent to the thin film.

18. The sensor device of claim 1, further comprising an antenna operable for transmitting measured data related to the shift in the magnetostrictive resonance frequency of the thin film from the first magnetostrictive resonance frequency to the second magnetostrictive resonance frequency to an external contactless data logger.

19. A method for fabricating a contactless sensor device operable for sensing water vapor or a predetermined chemical vapor, the method comprising:
providing a thin film, wherein providing the thin film comprises:
providing a soft magnetic layer;
disposing a sensing layer directly or indirectly adjacent to the soft magnetic layer, wherein the sensing layer comprises one of a nanostructured layer and a self-assembled monomolecular layer;
wherein the thin film has a first mass, a first density, and a first magnetostrictive resonance frequency prior to the sensing layer adsorbing a predetermined amount of a predetermined vapor; and
wherein the thin film has a second mass, a second density, and a second magnetostrictive resonance frequency subsequent to the sensing layer adsorbing the predetermined amount of the predetermined vapor;
disposing at least one microheater between the sensing layer and the soft magnetic layer;
disposing a driving coil indirectly adjacent to and at a predetermined distance from the thin film, the driving coil operable for generating an alternating-current magnetic field used to query a shift in the magnetostrictive resonance frequency of the thin film from the first magnetostrictive resonance frequency to the second magnetostrictive resonance frequency; and
disposing a measuring coil indirectly adjacent to and at a predetermined distance from the thin film, the measuring coil operable for measuring and quantifying the shift in the magnetostrictive resonance frequency of the thin film from the first magnetostrictive resonance frequency to the second magnetostrictive resonance frequency.

20. The method of claim 19, wherein the thin film has an initial thickness of between about 100 nm and about 5 mm.

21. The method of claim 19, wherein the sensing layer comprises a plurality of nanoparticles.

22. The method of claim 21, wherein the plurality of nanoparticles comprise at least one of a plurality of nanorods, a plurality of nanotubes, and a plurality of nanofibers.

23. The method of claim 19, wherein the sensing layer comprises a material selected from the group consisting of a zeolite, a polyelectrolyte, a porous ceramic, an aluminosilicate, carbon, and a combination comprising at least one of the foregoing materials.

24. The method of claim 19, wherein the sensing layer has an initial thickness of between about 1 nm and about 1 mm.

25. The method of claim 19, wherein the soft magnetic layer comprises a material selected from the group consisting of $Fe(x)Ni(y)P(z)B(n)$, $Fe(x)Tb(y)Dy(z)$, $Fe(x)Si(y)$, and a combination comprising at least one of the foregoing materials.

26. The method of claim 19, wherein the soft magnetic layer has an initial thickness of between about 100 nm and about 1 mm.

27. The method of claim 19, wherein disposing the sensing layer directly adjacent to the soft magnetic layer comprises growing the sensing layer on a surface of the soft magnetic layer.

28. The method of claim 19, wherein disposing the sensing layer directly adjacent to the soft magnetic layer comprises depositing the sensing layer on a surface of the soft magnetic layer.

29. The method of claim 19, wherein the driving coil and the measuring coil each comprise a planar coil integrated on a silicon wafer.

30. The method of claim 19, wherein the driving coil and the measuring coil are each disposed at an initial distance of between about 1 cm and about 0.5 m from the thin film.

31. The method of claim 19, further comprising providing a correlation algorithm operable for correlating the measured and quantified shift in the magnetostrictive resonance frequency of the thin film from the first magnetostrictive resonance frequency to the second magnetostrictive resonance frequency to an amount of the predetermined vapor present in an environment surrounding the sensor device.

32. The method of claim 19, wherein the predetermined vapor comprises one of water vapor and a predetermined chemical vapor.

33. The method of claim 19, further comprising disposing an adhesion layer on a surface of the soft magnetic layer prior to disposing the sensing layer indirectly adjacent to the soft magnetic layer, wherein the adhesion layer comprises at least one of a polymer layer and a metal layer.

34. The method of claim 19, further comprising disposing a plurality of dielectric layers on a surface of the soft magnetic layer prior to disposing the sensing layer indirectly adjacent to the soft magnetic layer, wherein the at least one microheater and the plurality of dielectric layers are arranged in a sandwich configuration.

35. The method of claim 34, wherein each of the plurality of dielectric layers comprises a material selected from the group consisting of silicon nitride, silicon oxide, parylene, and polyimide.

36. The method of claim 19, wherein each microheater comprises a material selected from the group consisting of a metal thin film, a heavily-doped silicon thin film, and a silicon carbide thin film.

37. The method of claim 19, further comprising sputtering the thin film onto the surface of a substrate.

38. The method of claim 19, further comprising providing an antenna operable for transmitting measured data related to the shift in the magnetostrictive resonance frequency of the thin film from the first magnetostrictive resonance frequency to the second magnetostrictive resonance frequency to an external contactless data logger.

* * * * *